US00PP35884P2

(12) United States Plant Patent
Spruyt

(10) Patent No.: US PP35,884 P2
(45) Date of Patent: Jun. 25, 2024

(54) ***TRADESCANTIA* PLANT NAMED 'JS BRAINSTORM'**

(50) Latin Name: *Tradescantia virginiana*
Varietal Denomination: JS BRAINSTORM

(71) Applicant: Spruyt Select CommV, Buggenhout (BE)

(72) Inventor: Jan Spruyt, Buggenhout (BE)

(73) Assignee: Spruyt Select CommV (NL)

( * ) Notice: Subject to any disclaimer, the term of this patent is extended or adjusted under 35 U.S.C. 154(b) by 0 days.

(21) Appl. No.: 18/229,027

(22) Filed: Aug. 1, 2023

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Tradescantia* plant named 'JS BRAINSTORM' is disclosed, characterized by abundant violet-purple flowers, blooming from June to November. Grass-like foliage with curving leaves of bluish-green with a purple hue. The new variety is a *Tradescantia*, typically used as an ornamental plant.

2 Drawing Sheets

Latin name of the genus and species: *Tradescantia virginiana.*

Variety denomination: 'JS BRAINSTORM'.

BACKGROUND OF THE INVENTION

The new cultivar is a product of chance discovery by the inventor, during the summer of 2017. The new variety was found in a cultivated field of *Tradescantia* 'Concord Grape', unpatented, in Buggenhout, Belgium.

Asexual reproduction of the new cultivar 'JS BRAINSTORM' by terminal cuttings was first performed in Buggenhout, Belgium at a commercial greenhouse during the spring of 2018 and has shown that the unique features of this cultivar are stable and reproduced true to type through successive generations.

SUMMARY OF THE INVENTION

The cultivar 'JS BRAINSTORM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'JS BRAINSTORM'. These characteristics in combination distinguish 'JS BRAINSTORM' as a new and distinct *Tradescantia* cultivar:

1. Long flowering period, from June to November.
2. Rich, continuous flowering.
3. Violet-purple flowers and attractive purple buds.
4. Grass-like foliage with curving leaves.
5. Bluish-green leaves with a purple hue.

PARENT COMPARISON

Plants of the new cultivar 'JS BRAINSTORM' are similar to plants of the parent variety in most horticultural characteristics, however, plants of the new cultivar 'JS BRAINSTORM' differ from in the following characteristics:

1. Plants of the new variety are shorter than plants of the parent variety.
2. Flower color of the new variety is darker purple than the flower color of 'Concord Grape'.
3. Flowering period is about 2 months longer than the flowering period of Concord Grape'.
4. The new variety produces more flowers than 'Concord Grape'.
5. Stems of the new variety are stronger than the stems of 'Concord Grape'.
6. Leaves of the new variety are bluish-green with a purple hue, while leaves of 'Concord Grape' are more green.

COMMERCIAL COMPARISON

Plants of the new cultivar 'JS BRAINSTORM' are similar to plants of the unpatented *Tradescantia* 'Leonora'. However, plants of the new cultivar differ in the following characteristics:

1. Flower color of the new variety is a darker purple than the flower color of this comparator.
2. Leaves of the new variety are bluish-green with a purple hue, while leaves of this comparator are lighter green.

BRIEF DESCRIPTION OF THE PHOTOGRAPHS

Figure 1:
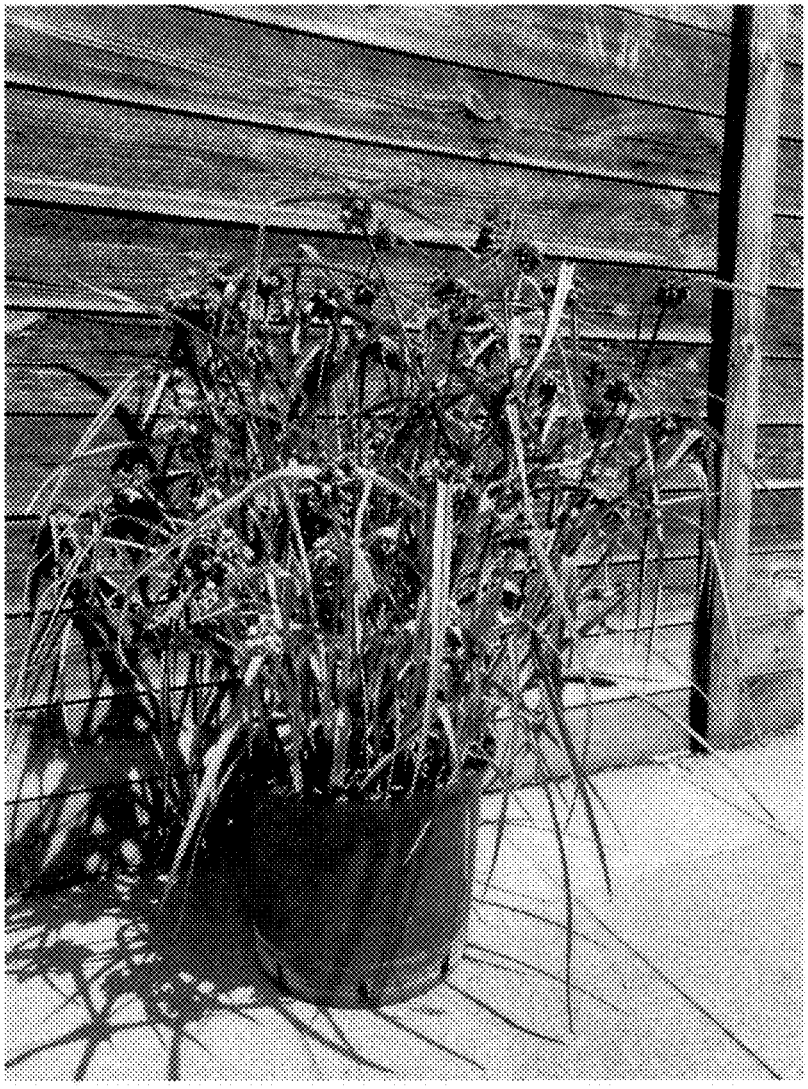

The accompanying photograph in FIG. 1 illustrates in full color a typical flowering plant of 'JS BRAINSTORM' grown outdoors in Ijsselmuiden, the Netherlands. The plant is approximately one year of age.

Figure 2:
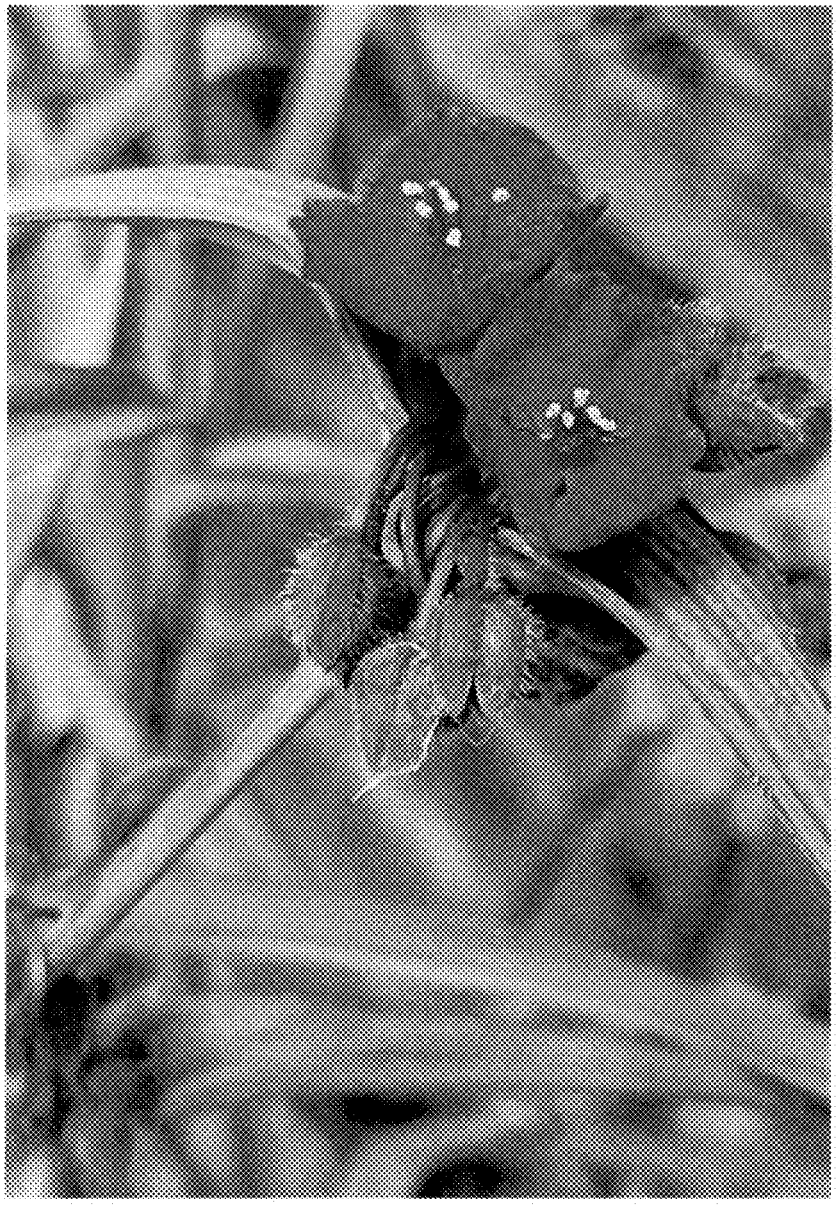

FIG. 2 illustrates a close up of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'JS BRAINSTORM' plants at one year of age, grown outdoors in Ijsselmuiden, the Netherlands. Measurements and numerical values represent averages of typical types.

Botanical classification: *Tradescantia virginiana* 'JS BRAINSTORM'.

ROOTS

Description of roots: Thick and somewhat fleshy. Light brown in color, not accurately measured with R.H.S. chart.

Time to initiate roots: About 10 days at approximately 20° C. in Summer.

PLANT

Plant type: Herbaceous perennial.
Container size: 28 cm.
Growth habit: Upright.
Height: 60 cm.
Plant spread: 72 cm.
Growth rate: Vigorous.
Quantity of lateral branches: 43.
Branching habit: Average 70° from horizontal.
Internode length: Up to 19 cm.
Stem:
- *Length*.—Average 56 cm.
- *Diameter*.—Up to 9 mm.
- *Shape*.—Round.
- *Color*.—RHS Green 137C.
- *Strength*.—Strong.
- *Texture*.—Glabrous.

Lateral branch:
- *Length*.—Average range 10 to 30 cm.
- *Diameter*.—4 to 7 mm.
- *Shape*.—Round.
- *Color*.—RHS Green 137C.
- *Strength*.—Strong.
- *Texture*.—Glabrous.

FOLIAGE

Leaf:
- *Arrangement*.—Alternate, simple.
- *Quantity per lateral branch*.—3.
- *Length*.—Up to 31 cm.
- *Width*.—1.8 cm.
- *Shape*.—Lanceolate.
- *Apex*.—Narrowly and long acute.
- *Base*.—Sheathing.
- *Attachment*.—Sessile.
- *Margin*.—Entire.
- *Texture upper and lower surfaces*.—Smooth, glabrous. Sparsely pubescent at the basal margins.
- *Color*.—Young foliage upper side: RHS Green 137A, heavily tinged with Purple N77A. Young foliage under side: RHS Green 137C, with Purple N77A at the margins. Mature foliage upper side: RHS Green 137C, with Purple N77A at the margins. Mature foliage under side: RHS Green 137C.

Venation:
- *Type*.—Parallel.
- *Color*.—RHS Green 137A.

FLOWER

Natural flowering season: June to November.
Inflorescence type: Single rotate flowers arranged in simple axillary and terminal clusters; freely flowering.
Quantity of inflorescences: 53 (some stems have 1, some 2 inflorescences).
Quantity of flowers: Up to 46 per cyme.
Lastingness of flowers: Typically 1 or 2 days.
Inflorescence size:
- *Length*.—Up to 5.5 cm.
- *Depth*.—About 3.5 cm.

Flower size:
- *Depth*.—0.6 cm.
- *Diameter*.—2.2 cm.

Petals:
- *Quantity*.—3.
- *Length*.—About 1.2 cm.
- *Width*.—About 1.6 cm.
- *Shape*.—Broadly ovate.
- *Margin*.—Entire.
- *Apex*.—Obtuse.
- *Base*.—Truncate.
- *Texture*.—Glabrous.
- *Color*.—Upper Surface: Near RHS Purple 83B. Lower Surface: RHS Purple N87A with 83B.

Bud:
- *Shape*.—Ovoid.
- *Height*.—About 9 mm.
- *Diameter*.—About 6 mm.
- *Color*.—RHS Green 137C, heavily tinged with Purple N77A.
- *Surface*.—Pubescent.

Sepals:
- *Quantity*.—3.
- *Length*.—About 9 mm.
- *Width*.—About 4 mm.
- *Shape*.—Ovate, cupped.
- *Color*.—Upper Surface: RHS Green 146C with Purple 77A (mostly at margins). Lower Surface: RHS Green 146C with Purple 77A (mostly at margins).
- *Texture*.—Outer Surface: Pubescent. Inner Surface: Glabrous.

Fragrance: None.
Peduncle:
- *Length*.—About 8 cm.
- *Diameter*.—About 4 mm.
- *Color*.—RHS Green 137C.
- *Texture*.—Glabrous.
- *Strength*.—Strong.

Pedicel:
- *Length*.—About 1.5 cm.
- *Diameter*.—About 1.5 mm.
- *Color*.—RHS Purple 77A with Green 137C.
- *Texture*.—Glabrous.
- *Strength*.—Moderately strong.

REPRODUCTIVE ORGANS

Gynoecium:
- *Pistil number*.—1.
- *Pistil length*.—1 cm.

*Stigma shape*.—Club-shaped.
*Stigma color*.—RHS White NN155A.
*Style length*.—About 8 mm.
*Style color*.—RHS Purple 83A.
*Ovary length*.—2 mm.
*Ovary color*.—RHS White NN155A.

Androecium:

*Stamen number*.—6.
*Stamen size*.—About 7 to 8 mm.
*Filament length*.—6 mm.
*Filament color*.—RHS Purple 83A.
*Anther shape*.—Reniform.
*Anther size*.—1.5 mm.
*Anther color*.—Near RHS Yellow 12A.
*Pollen quantity*.—Scarce.
*Pollen color*.—Near RHS Yellow 12A.

OTHER CHARACTERISTICS

Seeds and fruits: None observed to date.

Disease/pest resistance: No increased nor decreased resistance nor susceptibility to normal diseases and pests of *Tradescantia* has been observed. *Tradesncantia virginiana* is typically pest free, however, *Tetranychus urticae* may be found on plants, as well as garden snails (*Cornu aspersum*). Typical diseases of *Tradescantia* are Leaf spot (likely *Puccinia* sp. or the virus *Curvularia eragrostridis*) or *Pythium* sp. which may effect roots in overly moist conditions.

Temperature tolerance: Cold hardy to −20° C.

What is claimed is:

1. A new and distinct cultivar of *Tradescantia* plant named 'JS BRAINSTORM' as herein illustrated and described.

* * * * *